United States Patent [19]

Hobbs et al.

[11] 3,947,497

[45] Mar. 30, 1976

[54] LIQUID PHASE OXIDATION OF METHYL ETHYL KETONE TO FORM ACETIC ACID THEREFROM

[75] Inventors: Charles C. Hobbs, Corpus Christi, Tex.; Hendrik A. van't Hof, Brielle, Netherlands

[73] Assignee: Celanese Corporation, New York, N.Y.

[22] Filed: Jan. 4, 1974

[21] Appl. No.: 431,005

[52] U.S. Cl. ............................................. 260/541
[51] Int. Cl.² ......................................... C07C 51/28
[58] Field of Search ................................... 260/541

[56] References Cited
UNITED STATES PATENTS 2,005,183   6/1935   Fleming .............................. 260/541

*Primary Examiner*—Vivian Garner

[57] ABSTRACT

An improved process for the liquid phase oxidation of methyl ethyl ketone to acetic acid wherein increased carbon efficiencies are achieved by including formic acid and/or at least one formic acid-producing compound such as methyl formate in the reaction mixture. In a particularly advantageous embodiment, a liquid reaction feed mixture consisting essentially of from above about 50 to 90 percent methyl ethyl ketone and from about 10 up to about 50 percent of formic acid and/or the formic acid-producing compound is oxidized to acetic acid using air, cobalt acetate catalyst, and acetic acid reaction medium.

7 Claims, No Drawings

3,947,497

LIQUID PHASE OXIDATION OF METHYL ETHYL KETONE TO FORM ACETIC ACID THEREFROM

BACKGROUND AND SUMMARY OF THE INVENTION

1. Field of the Invention

This invention relates to improvements in the liquid phase oxidation of methyl ethyl ketone to form acetic acid therefrom.

2. Summary of the Prior Art

Carboxylic acids, and particularly acetic acid, have many uses. For example, acetic acid may be used as a solvent or reagent in the production of rubber, plastics, pharmaceuticals, dyes, insecticides and other organic and inorganic chemicals.

Carboxylic acids such as acetic acid may be produced by several processes including the liquid phase oxidation of various ketones such as methyl ethyl ketone. In general, such a liquid phase oxidation process involves the direct reaction of ketone with oxygen in a liquid carboxylic acid reaction medium. Typically, the carboxylic acid reaction product serves as the reaction medium to expedite separation and recovery of the reaction product. For example, when methyl ethyl ketone is oxidized to acetic acid, acetic acid is used as the reaction medium. See, for example, U.S. Pat. Nos. 2,005,183 and 2,299,013.

The presence of any formic acid in liquid phase oxidation processes for the production of acetic acid has long been thought to be undesirable not only because of the concomitant separation problems, but also because of the corrosive nature of formic acid. See, for example, U.S. Pat. Nos. 3,258,482; 2,913,492 and 2,659,746.

SUMMARY OF THE INVENTION

In accordance with the present invention, a liquid reaction mixture comprising methyl ethyl ketone and formic acid and/or at least one formic acid-producing compound is formed with methyl ethyl ketone being present in a predominant amount, and this liquid reaction mixture is oxidized with a gas comprising molecular oxygen to form an oxygenated reaction product mixture from which acetic acid reaction product is recovered.

The essence of a primary aspect of the present invention is the surprising discovery that methyl ethyl ketone can be oxidized in liquid phase to acetic acid with higher carbon efficiencies if the feedstock or liquid reaction mixture additionally comprises a formic acid-producing compound or formic acid itself. As indicated above, the presence or production of formic acid in liquid phase processes for the production of acetic acid has heretofore been considered undesirable. In the present invention, however, improved carbon efficiencies are achieved by deliberately causing the oxidation of methyl ethyl ketone with formic acid-producing compounds or formic acid itself.

Accordingly, a primary object of the present invention is to provide an improved process for the liquid phase oxidation of methyl ethyl ketone to form acetic acid therefrom.

Another more particular object of the present invention is to provide a novel liquid phase oxidation process for converting methyl ethyl ketone to acetic acid in efficiencies greater than that achieved by prior art processes.

Other objects, aspects, and advantages of the present invention will become apparent to one skilled in the art from the following description of the preferred embodiments.

DESCRIPTION OF THE PREFERRED EMBODIMENTS

As indicated above, a liquid reaction mixture comprising methyl ethyl ketone and formic acid and/or at least one formic acid-producing compound is formed with methyl ethyl ketone being present in a predominant amount, and this reaction mixture is oxidized with a gas comprising molecular oxygen to form an oxygenated reaction product mixture from which acetic acid reaction product is recovered.

When methyl ethyl ketone is referred to herein as being "present in a predominant amount," such reference means that there is more methyl ethyl ketone present in the liquid reaction mixture than any other single component or reactant which is oxidizable under conditions of liquid phase oxidation. In other words, there is more methyl ethyl ketone present than formic acid or any single formic acid-producing compound and any other oxidizable compound such as acetaldehyde or acetone. Typically, at least about 40 percent, based on the weight of oxidizable components, methyl ethyl ketone is present in the liquid reaction feed mixture. More typically, from above about 50 percent up to about 95 percent and even more typically above about 50 percent to about 90 percent methyl ethyl ketone is present in the liquid reaction feed mixture.

Any amount of formic acid or formic acid-producing compound is thought to increase the carbon efficiency of the liquid phase reaction in accordance with the present invention. Typically, at least about 5 percent based on the amount of oxidizable components, of formic acid or formic acid-producing compound is present in the liquid reaction mixture prior to oxidation. For example, the amount of formic acid or formic acid-producing compound may vary from about 5 up to about 50 percent more typically from about 10 up to about 50 percent of the liquid reaction feed mixture.

When a metal catalyst for the liquid phase oxidation reaction in the form of a carboxylic acid salt soluble in the liquid reaction mixture is used, and when formic acid itself is used to increase carbon efficiency, the formic acid should be present in the reaction mixture in an amount insufficient to precipitate the metal catalyst. For example, when cobalt acetate catalyst is used, any formic acid should be present in the reaction mixture in an amount less than about 5000 ppm, based on the total weight of the reaction mixture.

Any formic acid-producing compound, other than methyl ethyl ketone, may be used which will produce or give rise to sufficient formic acid in the liquid reaction mixture to increase carbon efficiency.

Suitable formic acid-producing compounds may include lower alkyl esters of formic or acetic acid, and lower alkanols.

For example, the lower alkyl esters may be of the formula $R_1COOR_2$ where $R_1$ is hydrogen or methyl and $R_2$ is an alkyl group of from 1 to 5 carbon atoms. Methyl formate, methyl acetate, and ethyl acetate are preferred.

The lower alkanols may be represented by the formula $R_3OH$, where $R_3$ is an alkyl group of from 1 to 5 carbon atoms. Methanol and ethanol are preferred.

The liquid reaction mixture may contain relatively minor amounts of other oxidizable components such as lower aliphatic aldehydes, e.g., acetaldehyde, and other lower aliphatic ketones, e.g., acetone.

As indicated above, the process of the present invention may be practiced by oxidizing a liquid reaction mixture of methyl ethyl ketone and one or more of the above-described formic acid or formic acid-producing compounds with a gas comprising molecular oxygen.

Air is commonly employed as the source of molecular oxygen, although a pure oxygen gas may also be employed. The molecular oxygen may be provided in at least a stoichiometrically sufficient amount to convert the material to be oxidized to acetic acid and to compensate or allow for the production of minor amounts of other carboxylic acids such as formic acid, as well as by-products such as carbon dioxide. The ratio of total feed of oxygen to total feed of organic starting material is a highly variable number which depends upon the specific composition of the feed, the desired products, and other process design factors. Typically, the oxygen-containing gas is bubbled through the liquid reaction mixture in an amount sufficient to prevent oxygen starvation which may be indicated by a low concentration of oxygen and/or a high ratio of carbon monoxide to carbon dioxide in the vent gas.

The oxidation reaction is conducted in the liquid phase, i.e., the material to be oxidized is in a liquid reaction medium. Typically, the liquid reaction medium is a solvent for the compounds to be oxidized and is relatively inert, i.e., does not react chemically at any significant rate under the conditions of oxidation. More typically, the reaction product or products serve as the solvent in which the reaction takes place. Acetic acid is preferred.

The reaction may be carried out at any temperature and pressure sufficient to maintain the liquid phase oxidation. For example, temperatures of about 50° to 200°C, preferably 75° to 150°C, and most preferably 110° to 140°C, may be used.

Superatmospheric pressure is generally required, and pressures of about 50 to 1.000 psia, preferably 75 to 300 psia, and typically 75 to 150 psia, may be used.

Reaction or reactor residence times may be from about 0.1 to 5 hours, more typically about 0.5 to 3 hours, and most typically about 1 to 2 hours.

The liquid phase oxidation process of the present invention is usually conducted in the presence of a catalyst. Liquid phase oxidation catalysts are well known and per se are not part of the present invention.

Typical liquid phase oxidation catalysts include metals from Groups 1$b$, 5$b$, 6$b$, 7$b$, 8$b$ and the Lanthanide series of the Periodic Table in the form of a compound soluble in the liquid reaction mixture. The Periodic Table referred to herein is the Periodic Table of the Elements appearing immediately after p. 948 of *Organic Chemistry*, by Morrison and Boyd; Allyn and Bacon, Inc. (1959 Ed.).

Non-limiting examples of such catalysts include the carboxylic acid-soluble compounds of cobalt, manganese, nickel, copper, cerium, praseodymium, neodymium, lanthanum, samarium, iron, mercury, chromium, antimony, uranium, molybdenum, terbium, tungsten, tantalum, columbium, vandium, zirconium, titanium, lead, tin, platinum, iridium, osmium, gold and silver, and particularly the salts of these metals with carboxylic acids such as, for example, acetic acid, propionic acid, butyric acid, isobutyric acid, valeric acid, benzoic acid and napthenic acid.

Cobalt acetate may be particularly advantageous and is preferred.

The above-described oxidation catalysts may be present during oxidation in an amount of about 1 to 50,000 ppm, preferably 100 to 5,000 ppm, and most preferably 200 to 2,000 ppm, based on the weight of solvent or liquid reaction medium.

The above-described liquid phase oxidation reaction may be carried out in any known stirred or non-stirred reactor or reaction vessel on a continuous, semi-continuous, or batch basis. A suitable tower reactor and its operation are described in U.S. Pat. No. 2,702,741, which is incorporated herein by reference.

The acetic acid reaction product may be recovered from the oxygenated reaction product mixture by various means known in the art, typically including distillation. Any acetic acid values contained in ester form in the reaction product may also be recovered by hydrolysis followed by solvent extraction and distillation as is well known to those skilled in the art. The acetic acid values in ester form may also be recycled to the reaction zone for further reaction. Typically, the oxygenated reaction product mixture contains formic acid and above about 50 percent acetic acid, based on the weight of the mixture. Formic acid may be present in the oxygenated product mixture in an amount of at least about 0.1 percent typically from about 0.1 to 0.5 percent.

The invention is additionally illustrated by the following examples; all parts, percentages and ratios are by weight in the examples, as well as in other parts of the specification and claims, unless otherwise indicated.

SPECIFIC EXAMPLES

Several runs (Nos. 2, 3 of Table I, Nos. 2 to 4 of Table II, and Nos. 2 to 4 of Table III) in accordance with the present invention were carried out in a reaction system comprising a vertical cylindrical reaction vessel provided with suitable fittings for feeding or injecting the reactants, including air, and catalyst solution (cobalt acetate dissolved in acetic acid) into the interior of the vessel, as well as a suitable outlet for recovery or take-off of a portion of the oxygenated reaction product mixture. A recycle conduit including a conventional centrifugal pump was also connected to the outlet for recycling a portion of the reaction mixture back into the reactor. By suitably adjusting valves in the various fittings, a ratio of recycled reaction mixture to recovered or collected reaction mixture of about 1000:1 was maintained. The reaction vessel was equipped with an electrical resistance heater to maintain reaction temperature; and vapors coming overhead from the liquid reaction mixture were condensed in a water-cooled condenser and returned to the liquid reaction mixture. A vent connected through a conventional cold trap to the upper end of the condenser was provided for removing any uncondensed vapors. In each of the runs, the reaction was allowed to "line-out," i.e., come to approximately steady-state conditions. Next, "timed run" was made, and during this timed run, all of the readings were taken and the volume and weight of the material fed to the reactor were measured. The liquid reactor feed and the catalyst solution were continuously supplied to the reactor and a portion of liquid oxygenated reaction product mixture was continuously withdrawn from the reactor, so as to maintain an approximately constant volume of liquid reaction mixture within the reactor during the timed runs. The reaction mixture was then analyzed using conventional procedures, and carbon efficiencies were calculated. Comparative runs (Nos. 1 to Tables I, II, and III) were carried out using the same apparatus and general procedure. Other data and the results of all of the runs are shown in TABLES I, II and III.

TABLE I[a]

| Run Number | 1 | 2 | 3 |
|---|---|---|---|
| Composition of reactor feed, % | | | |
|   Methyl ethyl ketone (MEK) | 85 | 80 | 75 |
|   Formic acid | — | 5 | 10 |
|   Other (substantially all acetic acid) | 15 | 15 | 15 |
| Composition of liquid reaction feed mixture (excluding acetic acid), % | | | |
|   MEK | 100 | 94 | 88 |
|   Formic acid | — | 6 | 12 |
| Co catalyst in reaction mixture, ppm | 1000 | 1000 | 1000 |
| Length of timed run, hrs. | 2 | 2 | 2 |
| Average reactor pressure[b], psia | 79 | 79 | 79 |
| Average temperature, °C | 130 | 130 | 130 |
| Carbon efficiency, % | 80.8 | 83.7 | 86.9 |

[a]The following quantities were the same in all of the runs
Volume of liquid in reactor plus recycle system, approximately 1000 ml.
Volume of liquid in reactor alone, approximately 800 ml.
Air rate, approximately 6.0 scfh = 3.6 scfh/in$^2$ cross-sectional area = 28 scfh/gal reactor liquid.
[b]Max. rec. pressure for equipment used.

TABLE II[a]

| Run Number | 1 | 2 | 3 | 4 |
|---|---|---|---|---|
| Composition of reactor feed,% | | | | |
|   Methyl ethyl ketone (MEK) | 26.6 | 36 | 27 | 19 |
|   Methanol (MeOH) | — | 9 | 3 | 2 |
|   Ethyl acetate (EtOAc) | — | — | 15 | 11 |
|   Ethanol (EtOH) | — | — | 7 | 5 |
|   Water (H$_2$O) | 7.2 | 5 | 10 | 7 |
|   Other (substantially all acetic acid) | 66.2 | 50 | 38[b] | 56 |
| Composition of liquid reaction feed mixture (excluding acetic acid and water), % | | | | |
|   Methyl ethyl ketone | 100 | 80 | 52 | 51 |
|   Methanol | — | 20 | 6 | 5 |
|   Ethyl acetate | — | — | 29 | 30 |
|   Ethanol | — | — | 13 | 14 |
| Co catalyst in reaction mixture, ppm | 1000 | 1000 | 1000 | 1000 |
| Length of timed run, hrs. | 2 | 2 | 2 | 2 |
| Average reactor pressure[c], psia | 79 | 79 | 79 | 79 |
| Average temperature, °C | 130 | 130 | 130 | 130 |
| Carbon efficiency, % | 85.2 | 92.0 | 91.8 | 89.5 |

[a]The following quantities were the same in all of the runs
Volume of liquid in reactor plus recycle system, approximately 1000 ml.
Volume of liquid in reactor alone, approximately 800 ml.
Air rate, approximately 6.0 scfh = 3.6 scfh/in$^2$ cross-sectional area = 28 scfh/gal reactor liquid.
[b]Substantially all acetic anhydride.
[c]Max. rec. pressure for equipment used.

TABLE III[a]

| Run Number | 1 | 2 | 3 | 4 |
|---|---|---|---|---|
| Composition of reactor feed, % | | | | |
|   Methyl ethyl ketone (MEK) | 85 | 59.5 | 51 | 47 |
|   Ethanol (EtOH) | — | 30 | — | — |
|   Acetaldehyde (AcH) | — | — | 20 | 5 |
|   Methyl formate | — | — | 20 | — |
|   Ethyl acetate | — | — | — | 40 |
|   Other (substantially all acetic acid) | 15 | 10.5 | 9 | 8 |
| Composition of liquid reaction feed mixture (excluding acetic acid), % | | | | |
|   Methyl ethyl ketone | 100 | 66.5 | 56 | 51 |
|   Ethanol | — | 33.5 | — | — |
|   Acetaldehyde | — | — | 22 | 5 |
|   Methyl formate | — | — | 22 | — |
|   Ethyl acetate | — | — | — | 44 |
| Co catalyst in reaction mixture, ppm | 1000 | 1000 | 1000 | 1000 |
| Length of timed run, hrs. | 2 | 2 | 2 | 2 |
| Average reactor pressure[b], psia | 79 | 79 | 79 | 79 |
| Average temperature, °C | 130 | 130 | 130 | 130 |

TABLE III[a] — Continued

| Run Number | 1 | 2 | 3 | 4 |
|---|---|---|---|---|
| Carbon efficiency, % | 85.0 | 88.0 | 95.3 | 85.1 |

[a] The following quantities were the same in all of the runs
Volume of liquid in reactor plus recycle system, approximately 1000 ml.
Volume of liquid in reactor alone, approximately 800 ml.
Air rate, approximately 6.0 scfh = 3.6 scfh/in$^2$ cross-sectional area = 28 scfh/gal reactor liquid.
[b] Max. rec. pressure for equipment used.

As may be seen from TABLES I, II and III, the runs using methyl ethyl ketone and formic acid, or one or more formic acid-producing compounds, resulted in higher carbon efficiencies when contrasted with the initial comparative runs.

The principles, preferred embodiments, and modes of operation of the present invention have been described in the foregoing specification. The invention which is to be protected herein, however, is not to be construed as limited to the particular forms disclosed, since these are to be regarded as illustrative rather than restrictive. Variations and changes may be made by those skilled in the art without departing from the spirit of the present invention.

We claim:

1. A liquid phase oxidation process for the production of acetic acid from methyl ethyl ketone, which process is characterized by improved carbon efficiency and which comprises:
    a. forming a liquid reaction mixture comprising methyl ethyl ketone, and at least one of the group consisting of formic acid and formic acid-producing compounds selected from the group consisting of lower alkanols, lower alkyl acetates, and lower alkyl formates, with methyl ethyl ketone being present in a predominant amount in the mixture on the acetic acid-free basis and with said formic acid or formic acid-producing compound constituting at least about 5 percent up to about 50 percent of the oxidizable components of said mixture;
    b. oxidizing the liquid reaction mixture with cobalt acetate catalyst in acetic acid reaction solvent with a gas comprising molecular oxygen to form an oxygenated rection product mixture containing about 0.1 to 0.5 weight percent formic acid and,
    c. recovering acetic acid reaction product from the reaction product mixture.

2. The process of claim 1 wherein at least about 40 percent methyl ethyl ketone and at least about 5 percent formic acid-producing compound are present in the liquid reaction mixture.

3. The process of claim 2 wherein the lower alkyl acetates or formates are of the formula $R_1COOR_2$ wherein $R_1$ is hydrogen or methyl and $R_2$ is an alkyl group of from one to five carbon atoms.

4. The process of claim 2 wherein the lower alkanol is an alcohol represented by the formula $R_3$—OH, wherein $R_3$ is an alkyl group of from one to five carbon atoms.

5. A liquid phase oxidation process for the production of acetic acid from methyl ethyl ketone, which process is characterized by improved carbon efficiency and which comprises
    a. forming a liquid reaction feed mixture comprising from above about 50 percent of at least one of the group consisting of formic acid and formic acid-producing compounds selected from the group consisting of alcohols represented by the formula $R_3$—OH, wherein $R_3$ is an alkyl group of from one to two carbon atoms.
    b. oxidizing the liquid reaction mixture in acetic acid reaction solvent at a temperature of about 50° to 200°C and a pressure of about 50 to 1,000 psi with a gas comprising molecular oxygen and with cobalt acetate oxidation catalyst to form an oxygenated reaction product mixture comprising about 0.1 to 0.5 percent by weight of formic acid and above about 50 percent acetic acid and,
    c. recovering acetic acid reaction product from the reaction product mixture.

6. The process of claim 5 wherein the reaction temperature is from 75° to 150°C, and wherein the reaction pressure is from 75 to 300 psi.

7. A liquid phase oxidation process for the production of acetic acid from methyl ethyl ketone, which process is characterized by improved carbon efficiency and which comprises
    a. forming a liquid reaction feed mixture consisting essentially of from above about 50 up to about 90 percent methyl ethyl ketone, and from about 10 up to about 50 percent of one of the group consisting of formic acid and formic acid-producing compounds other than methyl ethyl ketone, the formic acid-producing compound being at least one member selected from the group consisting of methyl formate, methylacetate and ethyl acetate, and the liquid reaction mixture being in a solvent of acetic acid;
    b. oxidizing the liquid reaction mixture in the liquid phase at a temperature of about 110° to 140°C and at a pressure of about 75 to 150 psi with molecular oxygen and from 100 to 5,000 ppm of a cobalt acetate catalyst to form an oxygenated reaction product mixture comprising above about 50 percent acetic acid and about 0.1 to 0.5% formic acid, and
    c. recovering acetic acid reaction product from the reaction product mixture.

* * * * *

UNITED STATES PATENT AND TRADEMARK OFFICE
CERTIFICATE OF CORRECTION

PATENT NO. : 3,947,497
DATED : March 30, 1976
INVENTOR(S) : Charles C. Hobbs and Hendrik A. van't Hof It is certified that error appears in the above-identified patent and that said Letters Patent are hereby corrected as shown below:

In column 6, line 1, after "Nos. 1", in place of "to" read -- of --.

In column 8, line 16, after "50 percent" insert --up to about 95% methyl ethyl ketone and from about 5% up to about 50% --.

*Signed and Sealed this* twenty-second *Day of* June 1976

[SEAL]

Attest:

RUTH C. MASON
*Attesting Officer*

C. MARSHALL DANN
*Commissioner of Patents and Trademarks*